(12) United States Patent
Gwilliam et al.

(10) Patent No.: US 9,646,469 B2
(45) Date of Patent: May 9, 2017

(54) VISUAL AND TOUCH INTERACTION DISPLAY

(71) Applicant: The Board of Trustees of the Leland Stanford Junior University, Palo Alto, CA (US)

(72) Inventors: James C Gwilliam, Taylorsville, UT (US); Allison M Okamura, Mountain View, CA (US); Andrew A Stanley, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 110 days.

(21) Appl. No.: 14/770,440

(22) PCT Filed: Mar. 7, 2014

(86) PCT No.: PCT/US2014/021668
§ 371 (c)(1),
(2) Date: Aug. 25, 2015

(87) PCT Pub. No.: WO2014/164274
PCT Pub. Date: Oct. 9, 2014

(65) Prior Publication Data
US 2016/0005277 A1    Jan. 7, 2016

Related U.S. Application Data

(60) Provisional application No. 61/775,647, filed on Mar. 10, 2013.

(51) Int. Cl.
*H04B 3/36* (2006.01)
*G08B 6/00* (2006.01)
(Continued)

(52) U.S. Cl.
CPC ........... *G08B 6/00* (2013.01); *A61B 34/76* (2016.02); *G06F 3/016* (2013.01); *G09B 21/003* (2013.01);
(Continued)

(58) Field of Classification Search
CPC ... G06F 3/16; G06F 3/233; G06F 3/44; G06F 3/11; G06F 1/163; G06F 1/161; G09B 21/003
(Continued)

(56) References Cited

U.S. PATENT DOCUMENTS

| 5,496,174 A * | 3/1996 | Garner | G09B 21/003 434/113 |
| 8,648,819 B2 * | 2/2014 | Philipp | G06F 3/044 345/156 |

(Continued)

*Primary Examiner* — Hoi Lau
(74) *Attorney, Agent, or Firm* — Lumen Patent Firm

(57) ABSTRACT

A sensory display for experiencing rigidity and local shape in the display is provided. Rigidity and local shape of cells in an array of cells forming the display is controlled by three independent and different control mechanisms. Cell rigidity controllers control the rigidity of the cells. A shape array controller controls the shape of the array of cells. Cell pinning controllers controls the height of the cells. A computer control interface could control the respective control functionalities of each of the controllers. The display experience could be further enhanced with audio, images or video.

14 Claims, 8 Drawing Sheets

(51) Int. Cl.
*G06F 3/01* (2006.01)
*G09B 21/00* (2006.01)
*A61B 34/00* (2016.01)
*A61B 34/30* (2016.01)
*A61B 90/00* (2016.01)

(52) U.S. Cl.
CPC ......... *A61B 34/30* (2016.02); *A61B 2090/372* (2016.02)

(58) Field of Classification Search
USPC ............ 340/407.1, 407.2; 345/173, 174, 156
See application file for complete search history.

(56) References Cited

U.S. PATENT DOCUMENTS

| | | | |
|---|---|---|---|
| 8,781,791 B2* | 7/2014 | Panther | G06F 3/011 702/160 |
| 9,554,484 B2* | 1/2017 | Rogers | A61B 5/6806 |
| 2008/0153590 A1* | 6/2008 | Ombrellaro | A63F 13/02 463/30 |
| 2008/0248836 A1* | 10/2008 | Caine | G06F 1/1616 455/566 |
| 2009/0256817 A1* | 10/2009 | Perlin | G06F 3/0233 345/174 |
| 2010/0141407 A1* | 6/2010 | Heubel | G06F 1/163 340/407.1 |
| 2011/0025602 A1* | 2/2011 | Sivan | G09B 21/003 345/156 |
| 2011/0254672 A1* | 10/2011 | Ciesla | G06F 3/016 340/407.2 |
| 2011/0316798 A1* | 12/2011 | Jackson | G06F 3/016 345/173 |
| 2012/0243151 A1* | 9/2012 | Lynch | H04M 1/0202 361/679.01 |
| 2013/0275082 A1 | 10/2013 | Follmer | |
| 2016/0004309 A1* | 1/2016 | Modarres | G06F 3/016 345/173 |
| 2016/0005277 A1* | 1/2016 | Gwilliam | G06F 3/016 340/407.1 |

\* cited by examiner

Top view

Side view

VISUAL AND TOUCH INTERACTION DISPLAY

CROSS-REFERENCE TO RELATED APPLICATIONS

This application is a 371 of PCT/US2014/021668 filed on Mar. 7, 2014. PCT/US2014/021668 claims the benefit of US Provisional Application 61/775,647 filed on Mar. 10, 2013.

STATEMENT OF GOVERNMENT SPONSORED SUPPORT

This invention was made with Government support under contract no. W81XWH-11-C-0050 awarded by the U.S. Army Medical Research and Materiel Command. The Government has certain rights in the invention.

FIELD OF THE INVENTION

The invention relates to visual and tactile displays. In particular, the invention relates to displays for experiencing visual and touch interaction.

BACKGROUND OF THE INVENTION

Tactile displays provide a means to utilize the sense of touch as a mode of communication. Technology development for tactile displays is driven by a number of applications. In teleoperation scenarios, including robotic surgery and bomb disposal, a tactile display at the master side can help restore some of the haptic feedback that the user loses by not interacting directly with the environment on the slave side. For individuals with auditory or visual impairments, a tactile display can serve as a form of sensory substitution to physically convey some of the information normally perceived by the impaired sense. Additionally, a tactile display can increase the realism of a virtual reality by immersing more senses of the user with the interface. In medical simulation, a compelling tactile display can play a vital role in ensuring effective training. Haptics play an important role in a clinician's diagnoses and decision regarding many procedures. Palpation is often necessary to identify subcutaneous anatomical landmarks or to differentiate between similarly shaped objects. By including a tactile display, virtual reality-based simulation can help clinicians gain experience tuning their sense of touch prior to performing a procedure or diagnosis on an actual patient.

While the technologies to convey visual and auditory information, such as LCD screens and surround speakers, have advanced to provide almost indistinguishable replication of sights and sounds, the technologies to mimic haptic sensations lag relatively far behind. The challenges inherent in synthesizing compelling recreations of physical interactions might provide a likely explanation for the gap in sensory display technologies. High-quality haptic feedback requires not only accurate kinesthetic feedback and lower-frequency forces, but also realistic cutaneous feedback of finger pad contact area, textures, and high-frequency vibrations. Encountered-type tactile displays can aim to recreate realistic haptic sensations by producing physical environments for a user to explore directly with his or her hands. Unlike sight and hearing, touch is bidirectional in that the haptic sensations delivered by an environment depend not only on its physical state, but also on the manner of the user's interactions. A tactile display that more accurately mimics the shape of an environment does not suffice to realistically recreate the feel of that environment; it must also deform and respond accordingly to the user's applied forces and motions. The present invention advances the art of sensory display technology by providing sense of rigidity and local shape in a display.

SUMMARY OF THE INVENTION

The present invention provides a sensory display for sensing or experiencing rigidity and local shape in the display. An array of cells forms the display interacting surface. Each cell has a flexible membrane filled with a granular material, a fluid or a combination thereof. Examples of a granular material are coffee grounds, sand, glass beads, wood or metal chips, sawdust, dirt, salt, or flour. Examples of a fluid are water, oil, an electrorheological fluids or a magnetorheological fluid. A cell rigidity controller connected to the cell controls the rigidity of the cell independent of the other cells' rigidity. The type of cell rigidity controller depends on the fill material or fluid. Accordingly, for changing the rigidity of the cells, one could use a pneumatic control mechanism, a hydraulic control mechanism, and/or a mechanism that changes the electrical or magnetic field inside the cell.

A shape array controller controls the overall shape of the array of cells independent of the cell rigidity controllers. The shape array controller is connected to a chamber located underneath the array of cells and could be operated using a pneumatic or a hydraulic control mechanism to change of the overall shape of the array of cells.

Local shape of the display could further be controlled by controlling each of the cells independently using cell pinning controllers, which control the height of the cell independently of the other cells' height. The cell pinning controllers further control the height of the cells independently of the cell rigidity controller, and independently of the shape array controller to control the overall shape of the array of cells. In one example, the cell pinning controllers controls the height of one or more nodes whereby nodes are cell boundaries or bordering points between the cells.

A computer control interface could be used to control the respective control functionalities of each of the controllers, i.e. each of the cell rigidity controllers, the shape array controller, each of the cell pinning controllers. A computer could execute a computer program, e.g. a display program, to control these respective control functionalities (simultaneously or sequentially) as desired for the sensation experience that is intended. The display program could be synchronized with audio, an image or a video to further enhance the display sensation experience, where, for example, the image or the video sequence of images could be super-imposed on the display.

Each of the cells 110, e.g. the nodes (indicated by the black circle), is connected 414 to a cell pinning controller 412. A node is defined as any point in the array where cells are bordering or where cell boundaries occur.

Figure 5:
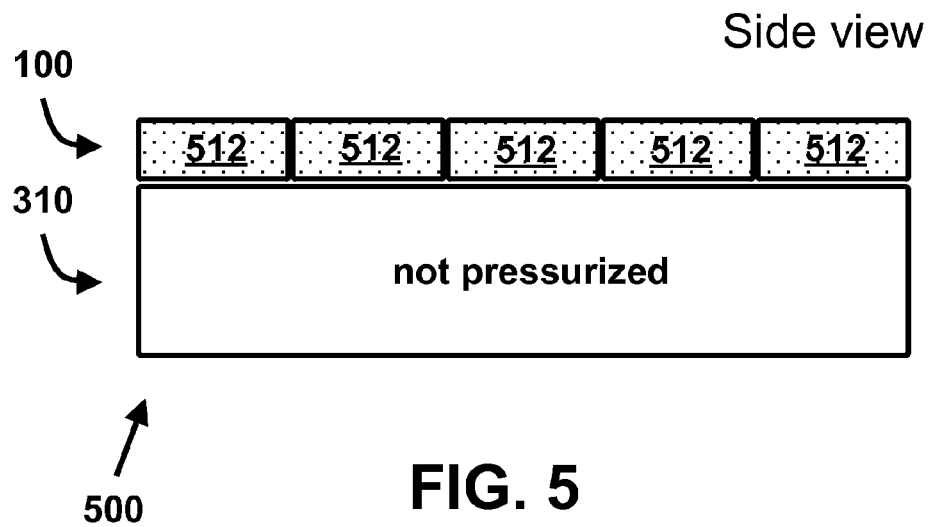

FIG. 5 shows a side view 500 of an array of cells 100 according to an exemplary embodiment of the invention. The cells 512 in the example are not vacuumed, and the chamber 310 is not pressurized. It is noted that in this example vacuuming is used to control rigidity of the cell(s) and pressurization is used to control shape. There are no nodes pinned in this example.

Figure 6:
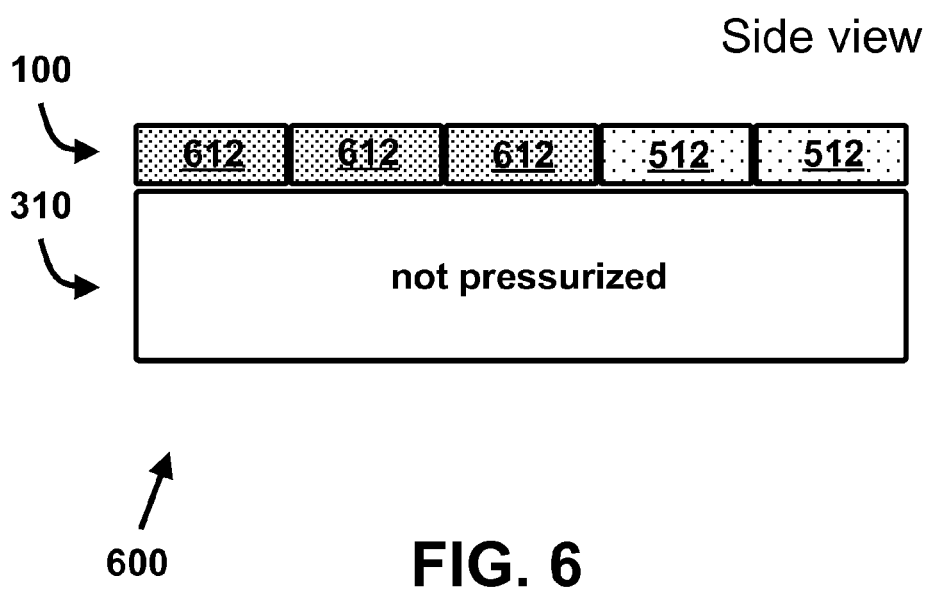

FIG. 6 shows a side view 600 of an array of cells 100 according to an exemplary embodiment of the invention. Cells 512 in the example are not vacuumed, whereas cells 612 are vacuumed. The chamber 310 is not pressurized. It is noted that in this example vacuuming is used to control rigidity of the cell(s). There are no nodes pinned in this example.

Figure 7:
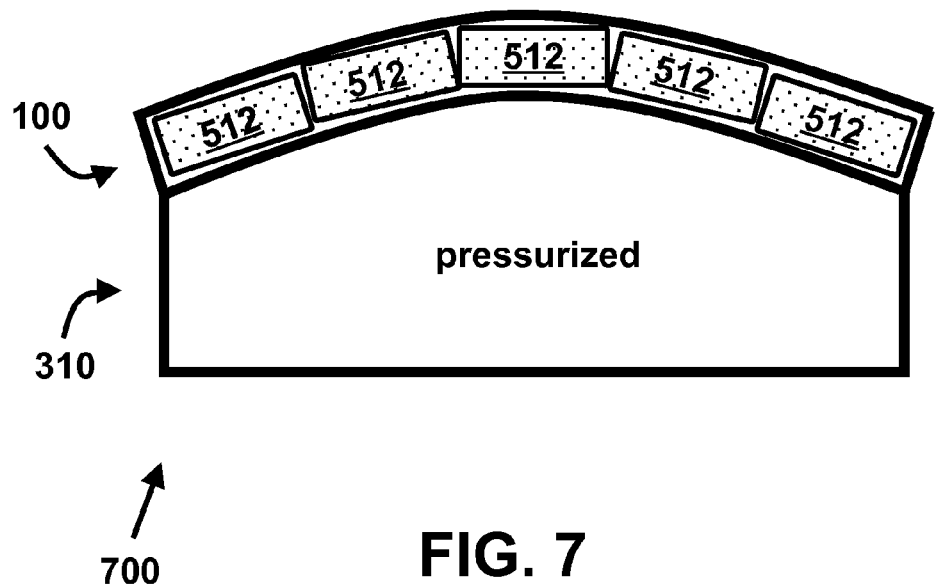

FIG. 7 shows a side view 700 of an array of cells 100 according to an exemplary embodiment of the invention. Cells 512 in the example are not vacuumed. The chamber 310 is pressurized. It is noted that in this example vacuuming is used to control rigidity of the cell(s) and pressurization is used to control shape. There are no nodes pinned in this example. Without the nodes pinned, all cells balloon as one.

Figure 8:
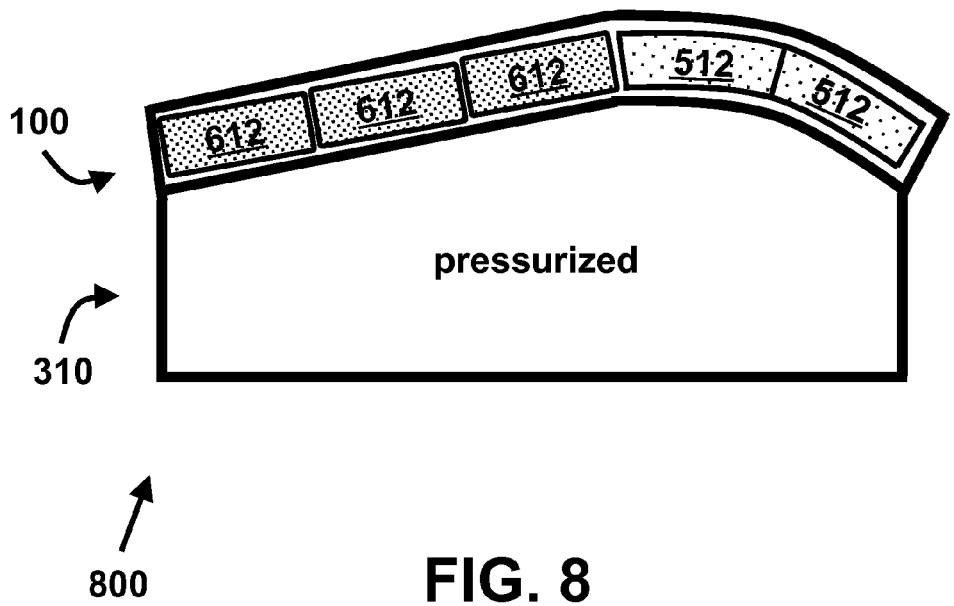

FIG. 8 shows a side view 800 of an array of cells 100 according to an exemplary embodiment of the invention. Cells 512 in the example are not vacuumed, whereas cells 612 are vacuumed. The chamber 310 is pressurized. It is noted that in this example vacuuming is used to control rigidity of the cell(s) and pressurization is used to control shape. There are no nodes pinned in this example. Without the nodes pinned, vacuumed cells 612 can still move when the chamber is pressurized, even though they stay relatively flat compared to non vacuumed cells 512 due to the fact that cells 612 are vacuumed to increase their rigidity. A node is defined as any point in the array where cells are bordering or where cell boundaries occur.

Figure 9:
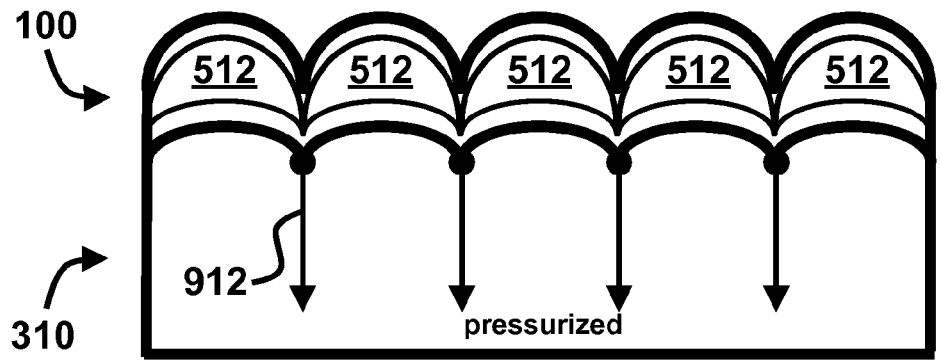

FIG. 9 shows a side view 900 of an array of cells 100 according to an exemplary embodiment of the invention. Cells 512 in the example are not vacuumed. The chamber 310 is pressurized. It is noted that in this example pressurization is used to control shape. Further in this example, the nodes (black circles) are pinned indicated by the arrows 912 representing a force sufficient to pin the node at the desired height. With the nodes pinned, the non-vacuumed cells 512 balloon separately. A node is defined as any point in the array where cells are bordering or where cell boundaries occur.

Figure 10:
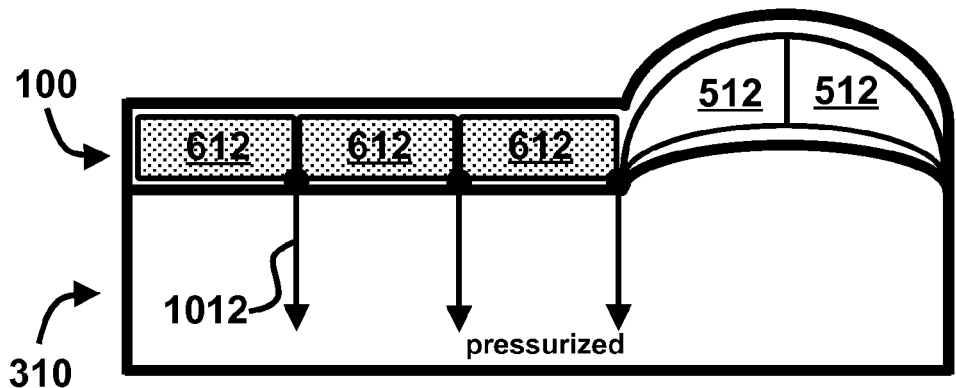

FIG. 10 shows a side view 1000 of an array of cells 100 according to an exemplary embodiment of the invention. Cells 512 in the example are not vacuumed, whereas cells 612 are vacuumed. The chamber 310 is pressurized. It is noted that in this example vacuuming is used to control rigidity of the cell(s) and pressurization is used to control shape. In this example, a subset of nodes (black circles) is pinned indicated by the arrows 1012 representing a force sufficient to pin the node at the desired height. Without the nodes of the non-vacuumed cells 512 pinned, the cells 512 balloon as one. With the nodes pinned of the vacuumed cells 612, cells 612 do not deform, i.e. relative to the non-vacuumed cells 512. A node is defined as any point in the array where cells are bordering or where cell boundaries occur.

Figure 11:
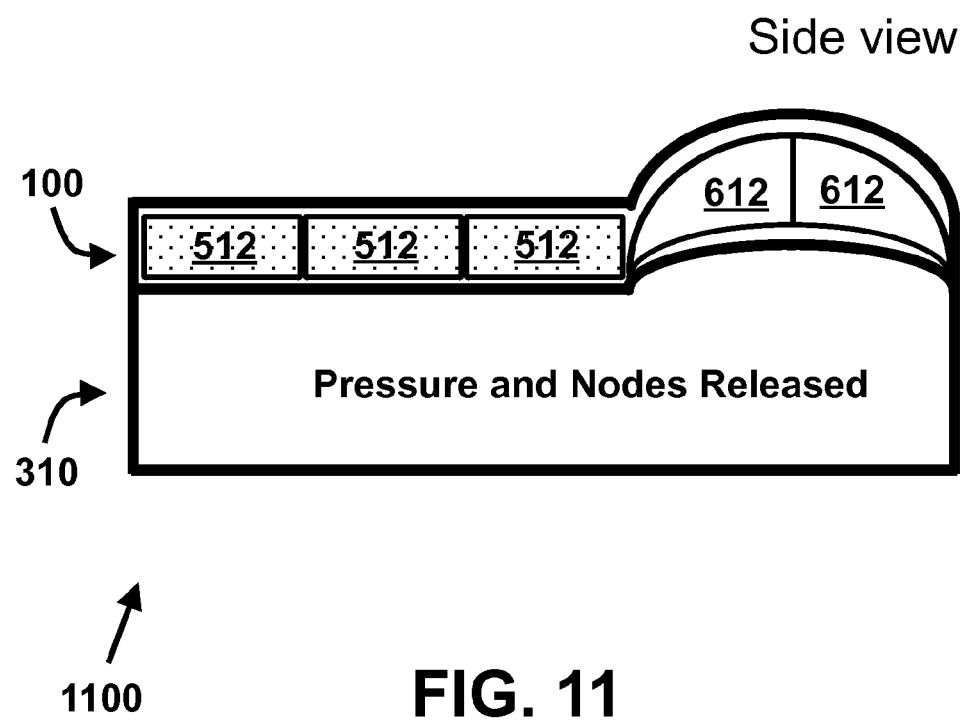
Figure 12:
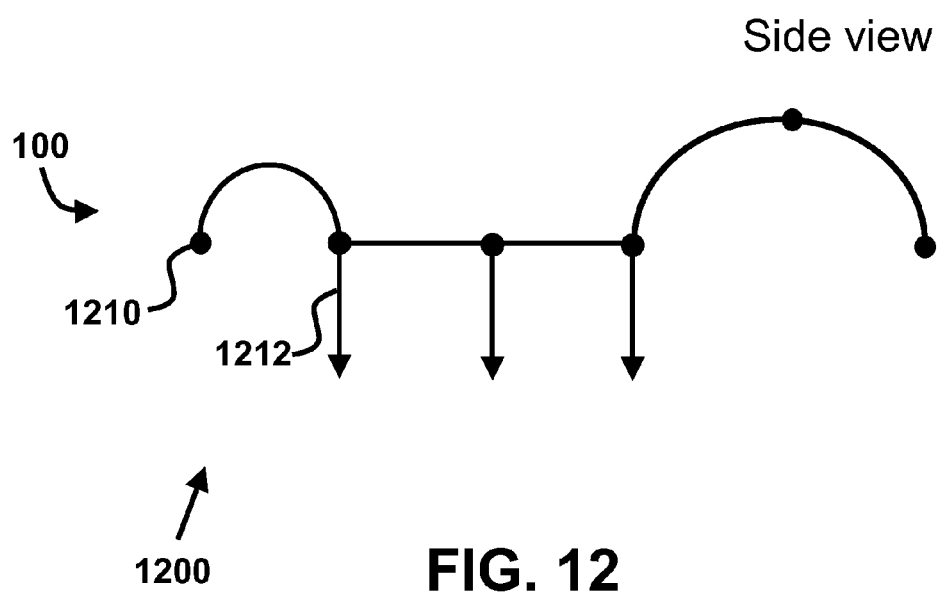
Figure 13:
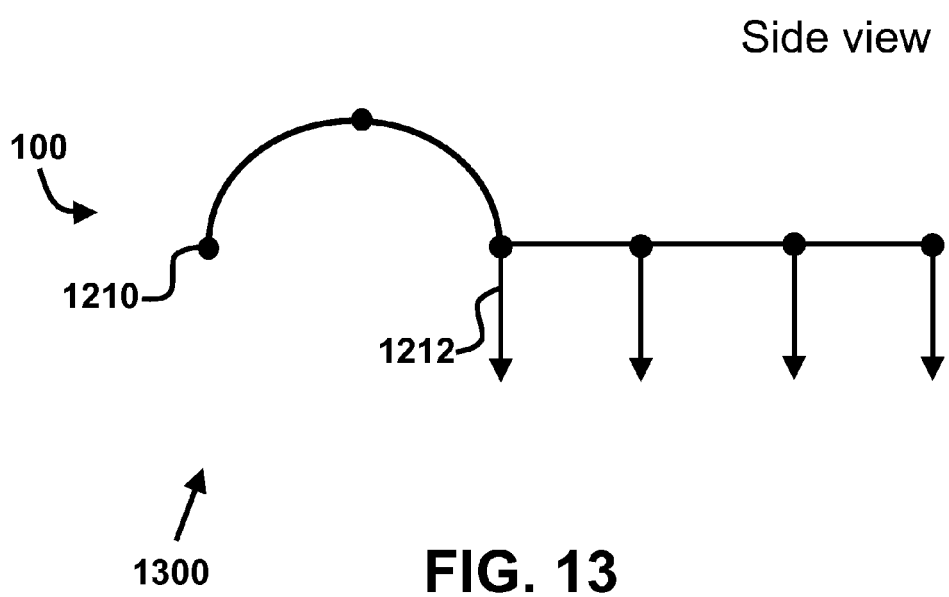
Figure 14:
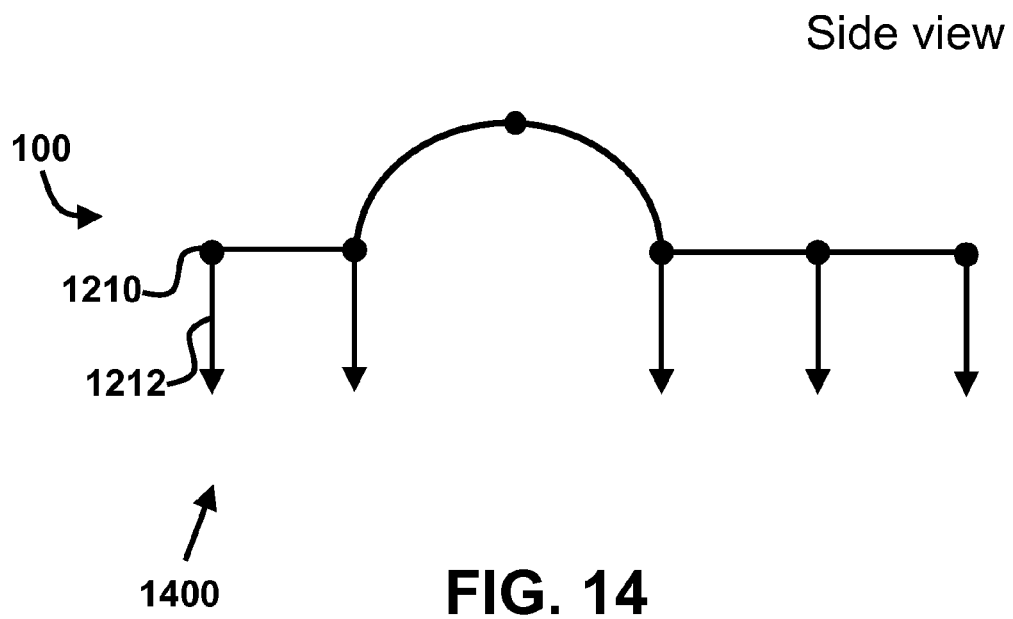
Figure 15:
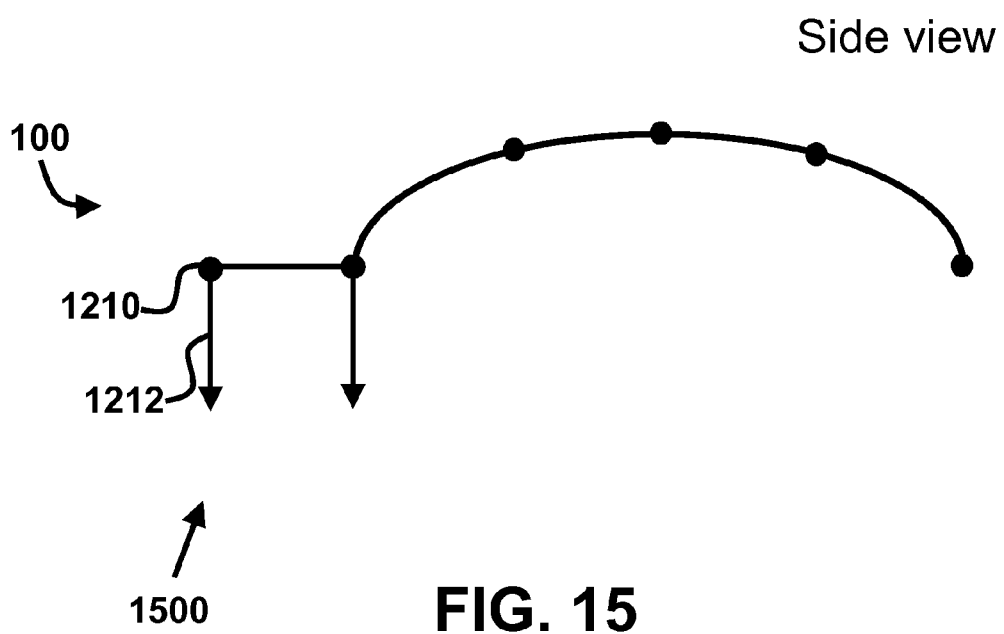

FIG. 11 shows a side view 1100 of an array of cells 100 according to an exemplary embodiment of the invention. FIG. 11 is a variation on FIG. 10; the cells have changed vacuum status, i.e. vacuumed cells 612 in FIG. 10 are now non-vacuumed cells 512 in FIG. 11 and vice versa. This example illustrates that vacuuming a deformed cell 512 of FIG. 10 now cell 612 in FIG. 11 will hold its shape so that the chamber pressure and nodes can be released. This creates one rigid lump (cells 612) in an otherwise soft surface (cells 512).

FIGS. 12-15 show side views 1200, 1300, 1400 and 1500 of different shape configurations formed by an array of cells 100 according to exemplary embodiments of the invention. In the same spirit as FIGS. 10-11, the configuration of each of the displays illustrates different examples where cells can be soft (relatively less rigid than other cells in the array) or rigid (relatively more rigid than other cells in the array) depending on the final chamber pressure. Nodes are indicated by 1210. Arrows 1212 representing a force sufficient to pin the node at the desired height.

DETAILED DESCRIPTION

A display with which a user can interact to experience visual and touch sensations is based on a two-dimensional array 100 of cells. The display is controlled by three different and independent control mechanisms to allow control of both deformable geometry and variable mechanical characteristics of the cells in the display. In other words, the display of this invention allows for independent control of geometry (i.e. shape) and mechanical characteristics (i.e. rigidity, firmness, stiffness, viscoelasticity, etc.) of each of the cells in the array of the display to enhance the sensation experience of the display by the user visually and by touch.

Rigidity Control

Cell rigidity controllers 210 are used to control the mechanical characteristics, e.g. rigidity, of the cells 110. Each cell 110 is independently connected 214 to a cell rigidity controller 212 to control the rigidity of that cell (e.g. stiffen or soften) independently of the other cell rigidity controllers, which allows for control of the surface of the display. In one example, each cell 110 has the flexible silicone membrane or surface and is filled with a granular material (e.g. coffee grounds, sand, glass beads, wood or metal chips, sawdust, dirt, salt, flour, or the like), a fluid (electrorheological or magnetorheological fluid, water, oil, or the like), or a combination thereof. The concept used for these cells is referred to as particle jamming and depending on the type of fill material different control mechanisms can be used to control and vary the rigidity of the cells and therewith the user experience of the cells.

- In case the cell is filled with a granular material or a combination of granular material and a fluid, the cell rigidity controller has a mechanism to change the pneumatic or hydraulic pressure inside the cell. A change in cell pneumatic or hydraulic pressure will then result in a change of rigidity of the cell as shown in the figures.
- In case the cell is filled with a fluid, the cell rigidity controller has a mechanism to change the hydraulic pressure inside the cell. A change in cell hydraulic pressure will then result in a change of rigidity of the cell.
- In case the cell is filled with an electrorheological fluid, the cell rigidity controller has a mechanism to change the electrical field inside the cell. A change in cell electrical field will then result in a change of rigidity of the cell as a result of a change in viscosity of the fluid. These fluids can increase their viscosity under application of an electric field to the point that they become viscoelastic solids.

In case the cell is filled with a magnetorheological fluid, the cell rigidity controller has a mechanism to change the magnetic field inside the cell. A change in cell magnetic field will then result in a change of rigidity of the cell as a result of a change in viscosity of the fluid. These fluids can increase their viscosity under application of a magnetic field to the point that they become viscoelastic solids.

Figure 1:
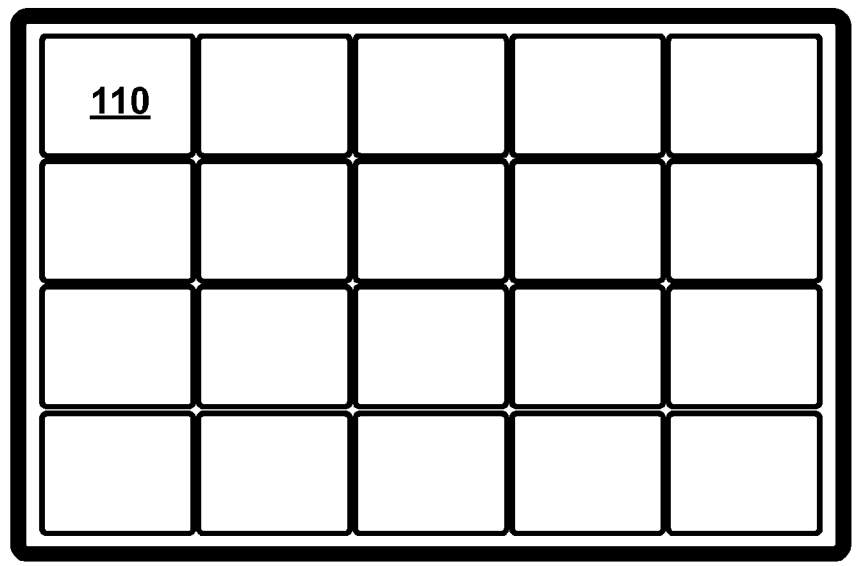
FIG. 1 shows a top view of a display with a plurality of cells 110 in a two-dimensional array 100 according to an exemplary embodiment of the invention.
Figure 2:
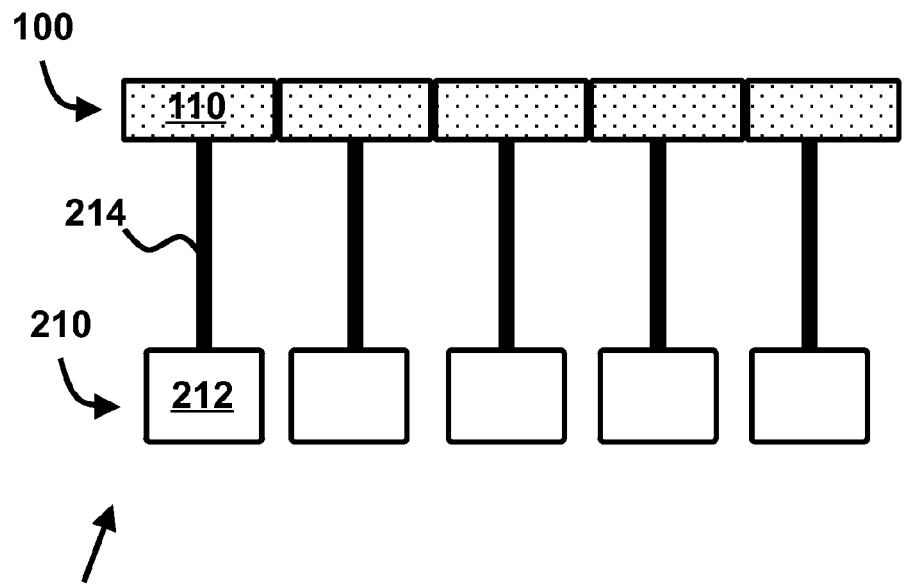
FIG. 2 shows a side view 200 of the cells 110 each connected 214 to a cell rigidity controller 212 according to an exemplary embodiment of the invention.

FIG. 1 shows each cell 110 with a rectangular shape, however, any shape or shape size can be envisioned such as a circular shape, a hexagonal shape, or the like. It is, however, preferred that the gaps between the cells from a top view perspective are minimized to optimize the surface resolution and variability of the interaction sensations. The surface resolution of the display is also a function of the number of cells in the array and the size or area of the cells (i.e. pixels). The array of cells 100 could have a top and bottom flexible (e.g. silicone) layer to provide a smooth (or smoother) surface (e.g. shown in FIGS. 7-11), however those additional layers are optional as long as the boundaries of the cells 110 are connected forming the array 100.

Shape Control I

Figure 3:
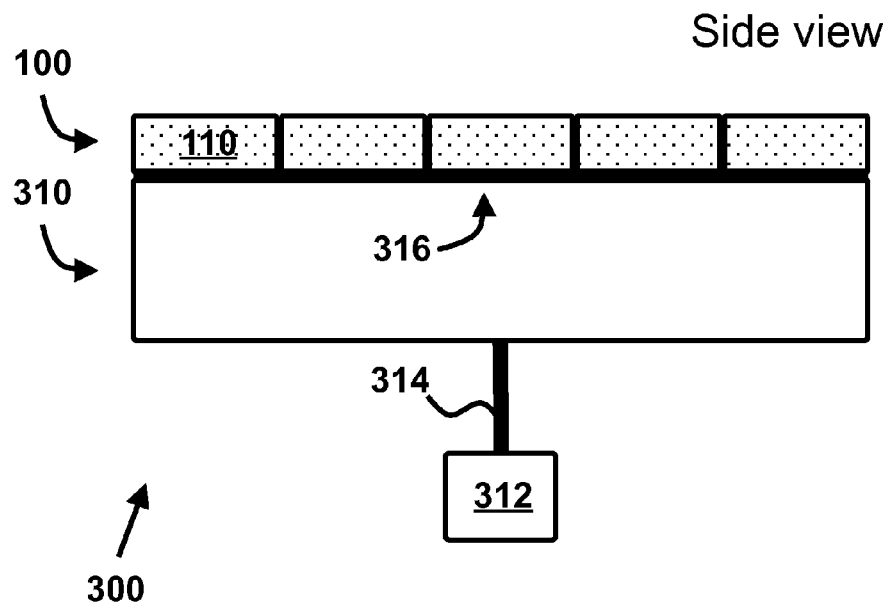
FIG. 3 shows a side view 300 of an array of cells 100 and a chamber 310 according to an exemplary embodiment of the invention. The chamber is connected 314 to a shape array controller 312.
Figure 4:
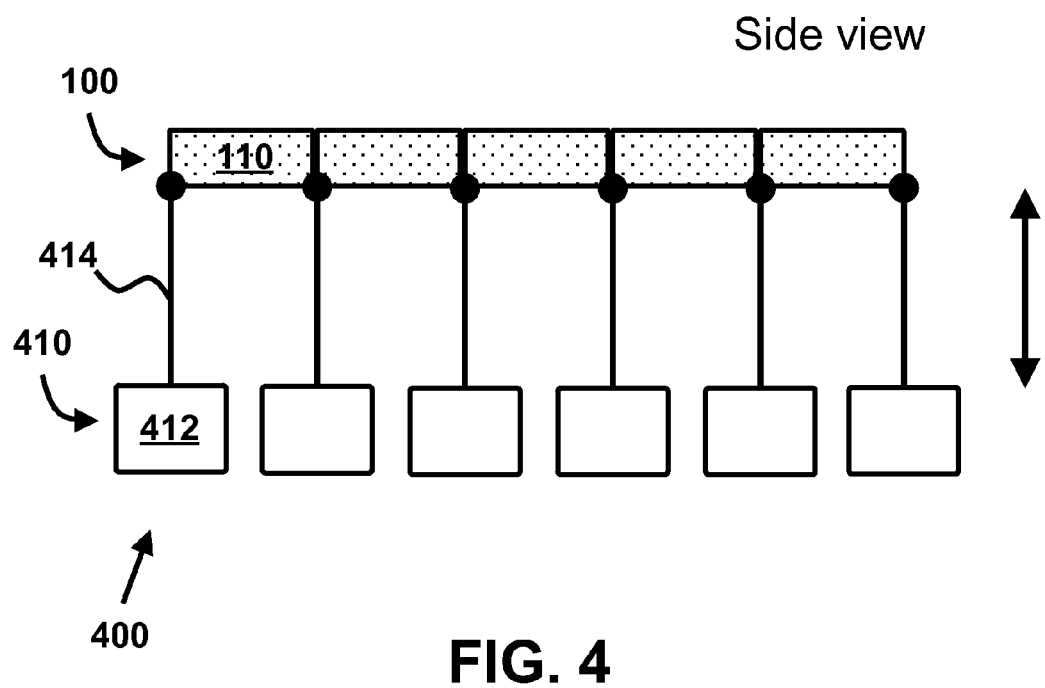
FIG. 4 shows a side view 400 of an array of cells 100 according to an exemplary embodiment of the invention.

A shape array controller 312 is connected 314 to a chamber 310, which is located underneath the array of cells 100 (FIG. 3). The goal of the shape array controller 312 is to deform, i.e. change the shape, of the cells. The extent of cell deformity in the array depends on the rigidity state of the individual cells (e.g. FIGS. 7-8).

In one example, the array of cells is held together by a flexible membrane 316 (e.g. a silicone membrane) that seals or clamps over chamber 310 (this could be a separate membrane or the interconnected flexible membrane structure of array 110 that is over chamber 310). The shape array controller could have a mechanism to change pneumatic pressure inside the chamber (e.g. positive or negative pressure). A change in chamber pneumatic pressure will then result in a change the force applied underneath the array of cells via flexible membrane 316 resulting in a change of the shape of the cells to establish surface deformation of the array.

The shape array controller is controlled independently of the cell rigidity controllers. A positive chamber pressure beneath the surface of the array would create convex (ballooning) deformations, whereas negative chamber pressure beneath the surface of the array would create concave deformations. In a different control mechanism than pneumatic, one could use a closed hydraulic system of fluid underneath the surface of the array and pressure to the flexible surface 316 could be established by regulating the fluid volume in the chamber. For example a sealed piston acting as a moving wall of the chamber could force the flexible surface 316 of the display upward by moving into the chamber or downward by moving outwards.

Shape Control II

Another way to control the shape of the cells in the display is to control the height of a cell (i.e. the height of a boundary point, or points of a cell), which is referred to as cell pinning. The height of the cell can be controlled by various mechanical means. In one example, a force is applied to a node to control the height (FIGS. 9-10 and 12-15). Height is defined along an axis perpendicular to the surface as shown in FIG. 1, which is the axis in line with the force vector 912 shown in FIG. 9. Depending on the type of control mechanism the node height can be control in both directions, i.e. up and down. A node is defined as any point in the array where cells are bordering or where cell boundaries occur. Each of the cells 110 can be independently connected 414 to a cell pinning controller 412 to control the height of the cell independently of the other cell pinning controllers 410, independently of the cell rigidity controller 212, and independently of the shape array controller 312. In other words, selectively pinning individual nodes to different heights allows selective combinations of cells into geometric features involving varying number of cells.

Various different mechanisms could be used to control the height.

Air cylinders could be connected to the nodes to pin selective nodes down when the air cylinders are pressurized.

Instead of using air cylinders one could pin the nodes at a certain height with solenoids by activating the solenoids or deactivating solenoids whose position in biased by a spring.

A motor could act as a winch to pin a node at any given height by pulling on a string or cable that is connected to a node of the surface.

A lever arm could be attached to a motor that could pull on a string, cable, or solid mechanical element that is connected rigidly or through a joint to a node on the surface.

In combination with a string, cable, or rigid rod that is connected to a node, a solenoid could be used to pin this string, cable, or rod in place, effectively holding that node of the surface at any given height.

Electrostatic forces could be generated to hold a node onto a substrate.

Electro magnets could be used to hold a node onto a substrate.

Lines connected to spring loaded reels could change the height of the nodes.

Computer Control

All controllers (cell rigidity, shape array and cell pinning) could be connected to a computer control interface to control their respective control functionalities and display various geometries that a user can experience visually or via touch. A computer program (e.g. a display control program) executable by a computer could control their respective control functionalities and generate a display experience. Adding an audio file, an image/photo or a video could further enhance the display sensation experience to the user. The audio, image or video could be synchronized to a display control program. The image and the video-images could be super-imposed on the display.

What is claimed is:

1. A display for experiencing visual and touch interaction, comprising:

(a) an array of cells, wherein each of the cells has a flexible membrane filled with a granular material, a fluid or a combination thereof, and wherein each of the cells is independently connected to a cell rigidity controller to control the rigidity of the cell independently of the other cell rigidity controllers;

(b) a chamber located underneath the array of cells, wherein the chamber is connected to a shape array controller to control the overall shape of the array of cells independently of the cell rigidity controllers controlling the rigidity of the cells; and (c) each of the cells independently connected to a cell pinning controller to control the height of the cell independently of the other cell pinning controllers, independently of the cell rigidity controller to control the rigidity of the cell, and independently of the shape array controller to control the overall shape of the array of cells.

2. The display as set forth in claim 1, wherein each of the cell rigidity controllers comprises a mechanism to change the pneumatic pressure inside the cell, whereby a change in cell pneumatic pressure results in a change of rigidity of the cell.

3. The display as set forth in claim 1, wherein each of the cell rigidity controllers comprises a mechanism to change the hydraulic pressure inside the cell, whereby a change in cell hydraulic pressure results in a change of rigidity of the cell.

4. The display as set forth in claim 1, wherein each of the cell rigidity controllers comprises a mechanism to change the electrical field inside the cell, whereby a change in cell electrical field results in a change of rigidity of the cell.

5. The display as set forth in claim 1, wherein each of the cell rigidity controllers comprises a mechanism to change the magnetic field inside the cell, whereby a change in cell magnetic field results in a change of rigidity of the cell.

6. The display as set forth in claim 1, wherein the granular material is coffee grounds, sand, glass beads, wood or metal chips, sawdust, dirt, salt, flour, or a combination thereof.

7. The display as set forth in claim 1, wherein the fluid is water, oil, an electrorheological fluid, a magnetorheological fluid, or a combination thereof.

8. The display as set forth in claim 1, wherein the shape array controller comprises a mechanism to change pneumatic pressure inside the chamber, whereby a change in chamber pneumatic pressure results in a change of the overall shape of the array of cells.

9. The display as set forth in claim 1, wherein the shape array controller comprises a mechanism to change hydraulic pressure inside the chamber, whereby a change in chamber hydraulic pressure results in a change of the overall shape of the array of cells.

10. The display as set forth in claim 1, wherein the cell pinning controller controls the height of one or more nodes, wherein the nodes are cell boundaries or bordering points between the cells.

11. The display as set forth in claim 1, wherein each of the cell rigidity controllers, the shape array controller, each of the cell pinning controllers comprises a computer control interface to control their respective control functionalities.

12. The display as set forth in claim 1, wherein each of the cell rigidity controllers, the shape array controller, each of the cell pinning controllers are controlled by a computer program executable by a computer to control their respective control functionalities.

13. The display as set forth in claim 1, wherein each of the cell rigidity controllers, the shape array controller, each of the cell pinning controllers are controlled by a computer program executable by a computer to control their respective control functionalities, and wherein the computer program is synchronized with audio, an image or a video.

14. The display as set forth in claim 1, wherein each of the cell rigidity controllers, the shape array controller, each of the cell pinning controllers are controlled by a computer program executable by a computer to control their respective control functionalities, and wherein the computer program is synchronized with an image or a video sequence of images that are super-imposed on the display.

* * * * *